US00PP17941P3

(12) United States Plant Patent
van Kesteren

(10) Patent No.: US PP17,941 P3
(45) Date of Patent: Aug. 21, 2007

(54) *SEDUM* PLANT NAMED 'CRAZY RUFFLES'

(50) Latin Name: ***Sedum* hybrid**
Varietal Denomination: Crazy Ruffles

(75) Inventor: Marc van Kesteren, Noordwijkerhout (NL)

(73) Assignee: Th. Langeveld B.V., Lisse (NL)

( * ) Notice: Subject to any disclaimer, the term of this patent is extended or adjusted under 35 U.S.C. 154(b) by 55 days.

(21) Appl. No.: 11/233,666

(22) Filed: Sep. 23, 2005

(65) Prior Publication Data

US 2007/0074322 P1 Mar. 29, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of *Sedum, Sedum* 'Crazy Ruffles', a sport of *Sedum* 'Matrona', characterized by its unique foliage with leaf margins that are dentated and wavy for a ruffled effect. 'Crazy Ruffles' exhibits pink tinged stems, a compact plant habit, and blooms with cymes of light pink flowers in late summer through early fall.

2 Drawing Sheets

Botanical classification: *Sedum* hybrid.
Varietal denomination: 'Crazy Ruffles'.

BACKGROUND OF THE INVENTION

The present invention relates to a new and distinct cultivar of *Sedum* of hybrid origin and will be referred to hereafter by its cultivar name, 'Crazy Ruffles'. 'Crazy Ruffles' was derived from *Sedum* 'Matrona' (not patented). 'Matrona' is a hybrid of *Sedum* 'Atropurpeum' and *Sedum* 'Herbsfreude' (syn. *Sedum* 'Autumn Joy', not patented).

The inventor discovered the new cultivar, 'Crazy Ruffles', in a nursery in Noordwijkerhout, The Netherlands in 2000. 'Crazy Ruffles' was discovered as a naturally occurring whole plant mutation in a block of containers of *Sedum* 'Matrona' that were originally derived from stem cuttings.

Sedum 'Crazy Ruffles' is unique for its foliage in which the leaves have margins that are wavy and dentated resulting in a ruffled effect. The margins of the parent plant are entire and the leaf aspect is flat.

Asexual reproduction of the new cultivar was first accomplished by stem cuttings in Noordwijkerhout, The Netherlands in 2001 by the inventor. The characteristics of the new cultivar have been determined to be stable and are reproduced true to type in successive generations.

SUMMARY OF THE INVENTION

The following traits have been repeatedly observed and represent the characteristics of the new cultivar as observed on plants grown for three years outdoors in Noordwijkerhout, The Netherlands. These attributes in combination distinguish 'Crazy Ruffles' from other varieties of *Sedum* known to the inventor.

1. The leaves of 'Crazy Ruffles' have margins that are dentated and wavy for a ruffled effect. The parent plant, 'Matrona', has leaves with margins that are entire and the leave aspect is flat.
2. The stems of 'Crazy Ruffles' are a rosy brown color.

3. The plant habit of 'Crazy Ruffles' is compact reaching a height of about 50 cm and a spread of 40 cm.
4. 'Crazy Ruffles' blooms with compound cymes of light pink flowers from July to September in The Netherlands.

'Crazy Ruffles' is a unique *Sedum*. The closest comparison plants in addition to the parent plant would be *Sedum* 'Jaws' (U.S. Plant Pat. No. 17,322) and varieties that are also mutations of 'Matrona'. 'Jaws' is similar to 'Crazy Ruffles' in that the leaf margins are not entire, however 'Jaws' is a mutation of 'Herbsfreude' (not patented) and has leaves with serrated margins that are not wavy rather than the dentated wavy margins of 'Crazy Ruffles'. Other cultivars exist in commerce that are mutations of 'Matrona', however they have entire leaf margins. For example, 'Black Jack' (U.S. Plant Pat. No. 16,736) is unique for its dark purple foliage coloration.

BRIEF DESCRIPTION OF THE DRAWING

The plants and plant parts in the accompanying photographs depict a three-year old plant of 'Crazy Ruffles' as grown in a 23 cm container in The Netherlands.

The photograph in the top of the first sheet provides an overall view of the plant habit and foliage of 'Crazy Ruffles'.

The photograph on the bottom of the first sheet is a close up view of a typical leaf of 'Crazy Ruffles'.

The photograph on the second sheet shows a typical inflorescence of 'Crazy Ruffles'.

The colors in the photographs are as close as possible with the photographic and printing technology utilized. The color values cited in the detailed botanical description accurately describe the colors of the new *Sedum*.

DETAILED BOTANICAL DESCRIPTION

The following is a detailed description of a three year-old plant of the new cultivar as grown outdoors in a 23 cm container in full sun in Noordwijkerhout, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Crazy Ruffles' is a cultivar of *Sedum* of hybrid origin.

Parentage: Naturally occurring mutation of *Sedum* 'Matrona'. 'Matrona' is a hybrid of *Sedum* 'Atropurpeum' and *Sedum* 'Herbsfreude' (syn. *Sedum* 'Autumn Joy').

General description:

*Blooming period.*—July through September in The Netherlands, flowers are persistent.

*Plant habit.*—Herbaceous perennial, clump-forming, compact, and broadly upright.

*Growth rate.*—Moderate growth rate.

*Height and spread.*—About 50 cm in height, up to about 40 cm in width.

*Hardiness.*—Known to be hardy to at least USDA Zone 3.

*Culture.*—Prefers well-drained to moist soils in full sun to partial shade.

*Diseases and pests.*—No susceptibility or resistance to diseases or pests known to affect *Sedum* has been observed for 'Crazy Ruffles'.

*Root description.*—Fleshy.

Growth and propagation:

*Propagation.*—Stem cuttings.

*Root development.*—Rooted cuttings fully develop a 2.5 cm container in about 12 weeks when grown under greenhouse conditions with ambient light.

Stem description:

*Shape.*—Round, hollow, succulent.

*Stem color.*—144A to 144C on shaded side, 177B to 177C on sides with sun exposure.

*Stem strength.*—Strong.

*Stem size.*—Average of 8 mm in diameter and 50 cm in length.

*Stem surface.*—Glabrous with slight gloss.

*Internode length.*—Average of 4.9 cm in length.

*Branching.*—Stems arise from base, no lateral branching.

Foliage description:

*Leaf shape.*—Broadly elliptic to ovate.

*Leaf division.*—Simple.

*Leaf base.*—Obtuse.

*Leaf apex.*—Rounded to slightly acute.

*Leaf venation.*—Pinnate, visible but not prominent, not raised or recessed, upper surface; 138A and 148C near base, lower surface; 144A to 144B and 144C to 144D near base.

*Leaf margins.*—Conspicuously wavy and dentate, average of 3 teeth per cm, average length of teeth is 3 mm.

*Leaf attachment.*—Sessile.

*Leaf arrangement.*—Opposite.

*Leaf surface.*—Glabrous, slightly glaucous.

*Leaf color.*—Newly formed upper surface; intermediate between 138A and 141A and 144A near base, newly formed lower surface; 137C, mature upper surface; 137A to 137B with base 138A, mature lower surface; 137C.

*Leaf side.*—Size decreases in size towards apex, average of 10.4 cm in length and 5.7 cm in width.

Flower description:

*Inflorescence type.*—Compound cyme of numerous star-shaped flowers.

*Flower fragrance.*—None.

*Flower type.*—Star-shaped.

*Flower number.*—About 375 per inflorescence.

*Inflorescence size.*—About 14.3 cm in diameter and 6.5 cm in depth including peduncles.

*Flower size.*—About 9 mm in depth and 9 mm in width.

*Flower aspect.*—Upright to slightly outward.

*Flower color.*—Overall color is light pink due to white petals and pistils with pink apices.

*Peduncle.*—Held at about a 30° angle to stem, up to about 10 cm in length and 3 mm in width, color 177B to N199A, surface is glabrous, strong.

*Pedicel.*—Held at about a 30° angle to peduncle, about 4 mm in length and 0.8 mm in width, 191A in color, surface is glabrous, strong.

*Calyx.*—Sepals 5, campanulate in shape, sepals separate but fused at base, about 3 mm in depth and 4 mm in diameter.

*Sepal shape.*—Narrowly ovate.

*Sepal apex.*—Acute.

*Sepal base.*—Cuneate and fused.

*Sepal margin.*—Entire.

*Sepal size.*—3 mm in length, 1 mm in width.

*Sepal color.*—138B (upper and lower surface).

*Sepal surface.*—Glabrous (upper and lower surface).

*Corolla description.*—Petals 5, separate but fused at base, held upward and slightly spreading.

*Petal shape.*—Ovate.

*Petal apex.*—Acute.

*Petal base.*—Fused.

*Petal margin.*—Entire.

*Petal size.*—Average of 8.5 mm in length and 3 mm, tapering to a point at apex.

*Petal color.*—Upper and lower surface (opening and fully open) 64D to 65A with base 155A, color fades to 157D to 145D.

*Petal surface.*—Glabrous, both of surfaces.

*Bud shape.*—Ovate.

*Bud size.*—Up to 7 mm in length and 4 mm in width.

*Bud color.*—145C with tips tinged with 182C to 182D.

Reproductive organs:

*Gynoecium.*—5 Pistils, petaloid with a simple stigmatic surface, lanceolate in shape with attenuating tip, collectively flask-shaped, about 6 mm in length and 1.5 mm in width, style is 157A in color, stigma is 186A in color. Ovules comprised of a tiny scale at the base of each carp, inferior, 0.5 mm in diameter, 157A in color.

*Androcoecium.*—10 stamens, 5 stamens at base of petals and 5 stamens are free, free filaments are 6 mm in length and 155A in color, anthers are basifixed, flattened, broadly oblong, 0.5 mm in length and 199A in color, pollen in very low in abundance and 199B to 199C in color.

*Fruit.*—Follicle 200D in color, about 6 mm in length and 4 mm in width.

*Seed.*—Average of 10 seeds per fruit, 1 mm in diameter, 200A to 202A in color.

I claim:

1. A new and distinct cultivar of *Sedum* plant named 'Crazy Ruffles' as herein illustrated and described.

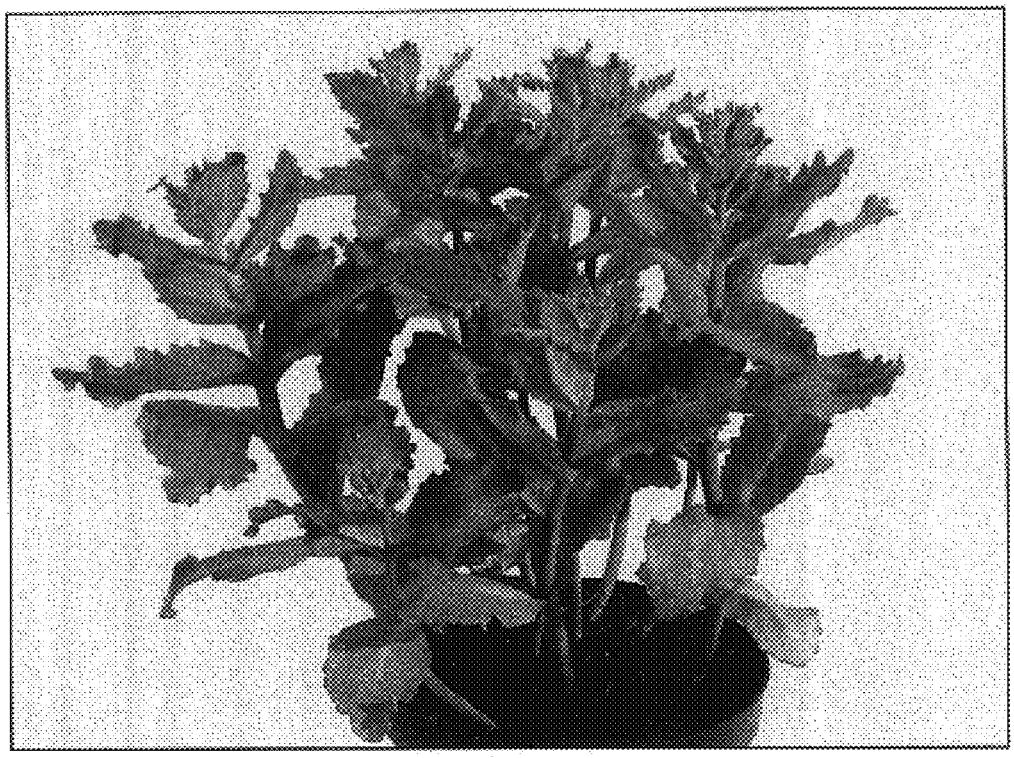
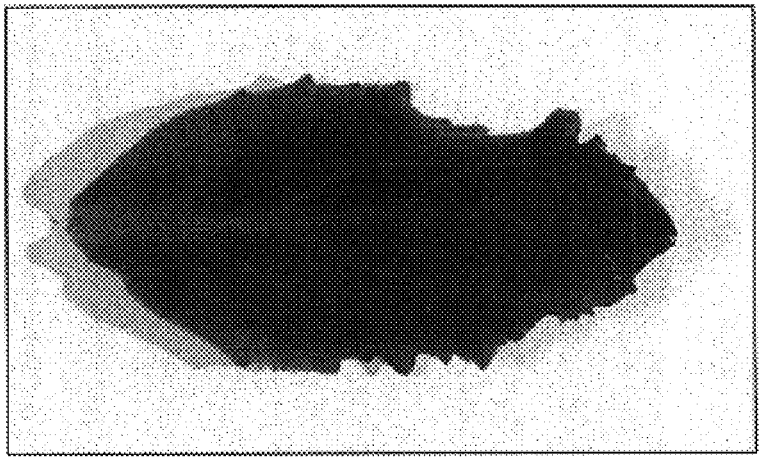

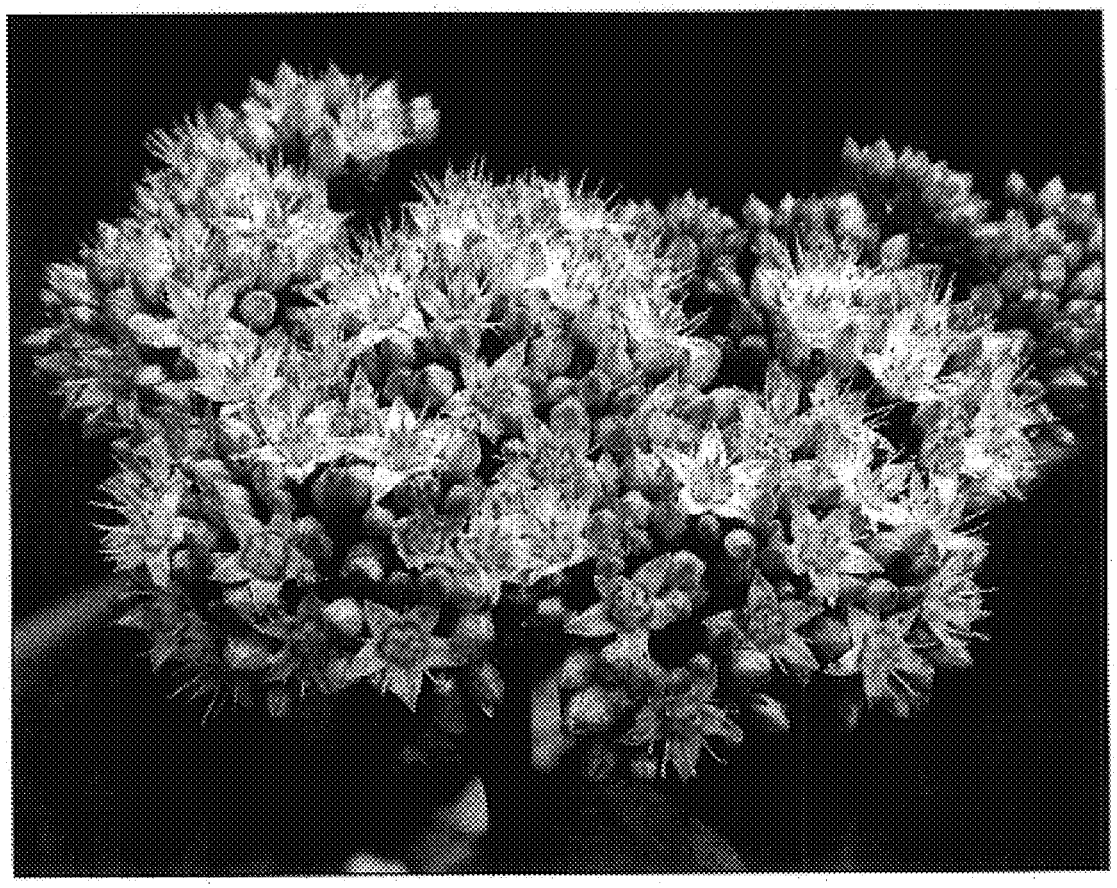

* * * * *